(12) United States Patent
Macevicz

(10) Patent No.: US 8,003,329 B2
(45) Date of Patent: Aug. 23, 2011

(54) MOLECULAR COUNTING BY COLOR-CODED MICELLES

(75) Inventor: Stephen C. Macevicz, Cupertino, CA (US)

(73) Assignee: Becton Dickinson & Company, Franklin Lakes, NJ (US)

( * ) Notice: Subject to any disclaimer, the term of this patent is extended or adjusted under 35 U.S.C. 154(b) by 20 days.

(21) Appl. No.: 12/460,835

(22) Filed: Jul. 23, 2009

(65) Prior Publication Data
US 2011/0020793 A1    Jan. 27, 2011

Related U.S. Application Data

(60) Provisional application No. 61/215,993, filed on May 12, 2009.

(51) Int. Cl.
*C12Q 1/68* (2006.01)
*C12P 19/34* (2006.01)

(52) U.S. Cl. .......................... 435/6; 435/91.2

(58) Field of Classification Search .................. None
See application file for complete search history.

(56) References Cited

U.S. PATENT DOCUMENTS

| | | | |
|---|---|---|---|
| 6,858,412 B2 | 2/2005 | Willis et al. | |
| 7,537,897 B2 | 5/2009 | Brenner et al. | |
| 2004/0005594 A1 | 1/2004 | Holliger et al. | |
| 2005/0079510 A1 | 4/2005 | Berka et al. | |
| 2005/0250147 A1 | 11/2005 | Macevicz | |
| 2007/0087362 A1 | 4/2007 | Church et al. | |
| 2007/0172873 A1* | 7/2007 | Brenner et al. | 435/6 |
| 2008/0212069 A1 | 9/2008 | Goldberg et al. | |

OTHER PUBLICATIONS

Hardenbol et al., "Multiplexed Genotyping with Sequence Tagged Molecular inversion probes" Nat. Biotechnology, 2003 21:673.
Lee et al., "Single-molecule enzymology of chymotrypsin using water-in-oil emulsion" Biophysical J., 88: 4303-4311 (2005).
Marras et al., "Multiplex detection of single-nucleotide variations using molecular beacons" Genet. Anal. 14: 151-156 (1999).
Mastrobattista et al., "High-Throughput Screening of enzyme libraries: in vitro evolution of a (beta)-galactosidase by fluorescence-activated sorting of double emulsions" Chemistry & Biology, (2005); 12: 1291-1300.
Musyanovych et al., "Miniemulsion droplets as single molecule nanoreactors for polymerase chain reaction" Biomacromolecules, 6: 1824-1828 (2005).
Nilsson et al., "Padlock probes: circularizing oligonucleotides for localized DNA detection" Science, 265: 2085-2088 (1994).
Tawfik et al., "Man-made cell-like compartments for molecular evolution" Nature Biotechnology, 16: 652-656 (1998).
Tyagi et al., "Molecular beacons: probes that fluoresce upon hybridization" Nature Biotechnology 14: 303-308 (1996).
Tyagi et al., "Multicolor molecular beacons for allele discrimination" Nature Biotechnology 16: 49-53 (1998).
Vet et al., "Multiplex detection of four pathogenic retroviruses using molecular beacons" Proc. Natl. Acad. Sci. 96: 6394-6399 (1999).
Zhang et al., Long-range polony haplotyping of individual human chromosome molecules Nat. Genetics (2006) 38:382.

* cited by examiner

*Primary Examiner* — Kenneth R. Horlick
*Assistant Examiner* — David Thomas
(74) *Attorney, Agent, or Firm* — David C. Scherer; Bozicevic, Field & Francis LLP

(57) ABSTRACT

The invention provides a method of determining ratios of target DNA molecules in a sample. A digital readout of the target DNA molecules is provided by converting ratios of target DNA molecules into equivalent ratios of amplifiable tags, which are, in turn, converted into ratios of color-coded micelles in an emulsion reaction. The micelles may be detected and counted by various methods, including by flow cytometers or slide-based imaging devices. The invention is useful for detection of relative expression levels of selected genes, gene copy number polymorphisms, allelic imbalance, relative levels of iRNAs, and related phenomena of scientific and medical interest.

8 Claims, 6 Drawing Sheets

MOLECULAR COUNTING BY COLOR-CODED MICELLES

CROSS-REFERENCE

This application claims the benefit of U.S. Provisional Application No. 61/215,993, filed May 12, 2009, which application is incorporated herein by reference.

BACKGROUND

The difference between health and disease frequently depends on whether or not certain biomolecules of an organism are within tightly controlled tolerances. This has led to an active search for quantitative molecular biomarkers to assess states of health and disease, e.g. Slamon et al, Science, 240: 1795-1798 (1988); Sidransky, Nature Reviews Cancer, 2: 210-219 (2002); Pinkel and Albertson, Ann. Rev. Genomics Hum. Genet., 6: 331-354 (2005); Stankiewicz and Lupski, Trends in Genetics, 18: 74-82 (2002); Hanna, Oncology, 61 (suppl 2): 22-30 (2001); Cronin et al, Am. J. Pathol., 164: 35-42 (2004); and the like. Although many techniques are available to measure amounts of biomolecules, they each have trade-offs with respect to sensitivity, selectivity, dynamic range, convenience, robustness, cost, and so on. For nucleic acid measurements, most techniques provide analog readouts, in that measured amounts are correlated with signal intensities, e.g. Pinkel and Albertson, Nature Genetics Supplement, 37: S11-S17 (2005); Lockhart et al, Nature Biotechnology, 14: 1675-1680 (1996). Digital measurements of polynucleotides have been made, where measured amounts are correlated with integral numbers of countable events, e.g. numbers of sequence tags; however, even though such measurements have significant statistical advantages, they are usually more difficult and expensive to implement, e.g. Brenner et al, Nature Biotechnology, 18:630-634 (2000); Velculescu et al, Science, 270: 484-487 (1995); Dressman et al, Proc. Natl. Acad. Sci., 100: 8817-8822 (2003); Audic and Claverie, Genome Research, 7: 986-995 (1997).

In view of the great interest, particularly in the cancer field, of the potential prognostic value of genomic copy number changes, the availability of a cost-effective technique for providing digital measurements of biomolecules would be highly desirable in many areas in the biomedical and biological sciences.

SUMMARY OF THE INVENTION

The invention is a method of determining ratios of target DNA molecules in a sample. A digital readout of the target DNA molecules is provided by converting ratios of target DNA molecules into equivalent ratios of amplifiable tags, which are, in turn, converted into ratios of color-coded micelles in an emulsion reaction. The micelles may be detected and counted by various methods, including by flow cytometers or slide-based imaging devices. The invention is useful for detection of relative expression levels of selected genes, gene copy number polymorphisms, allelic imbalance, relative levels of iRNAs, and related phenomena of scientific and medical interest.

DETAILED DESCRIPTION OF THE INVENTION

The practice of the present invention may employ, unless otherwise indicated, conventional techniques from molecular biology (including recombinant techniques), cell biology, immunoassay technology, microscopy, image analysis, and analytical chemistry, which are within the skill of the art. Such conventional techniques include, but are not limited to, detection of fluorescent signals, image analysis, selection of illumination sources and optical signal detection components, labeling of biological cells, and the like. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press); Murphy, Fundamentals of Light Microscopy and Electronic Imaging (Wiley-Liss, 2001); Shapiro, Practical Flow Cytometry, Fourth Edition (Wiley-Liss, 2003); Herman et al, Fluorescence Microscopy, $2^{nd}$ Edition (Springer, 1998); Hermanson, Bioconjugate Techniques, $2^{nd}$ Edition (Academic Press, 2008); all of which are herein incorporated in their entirety by reference for all purposes.

Figure 1A:
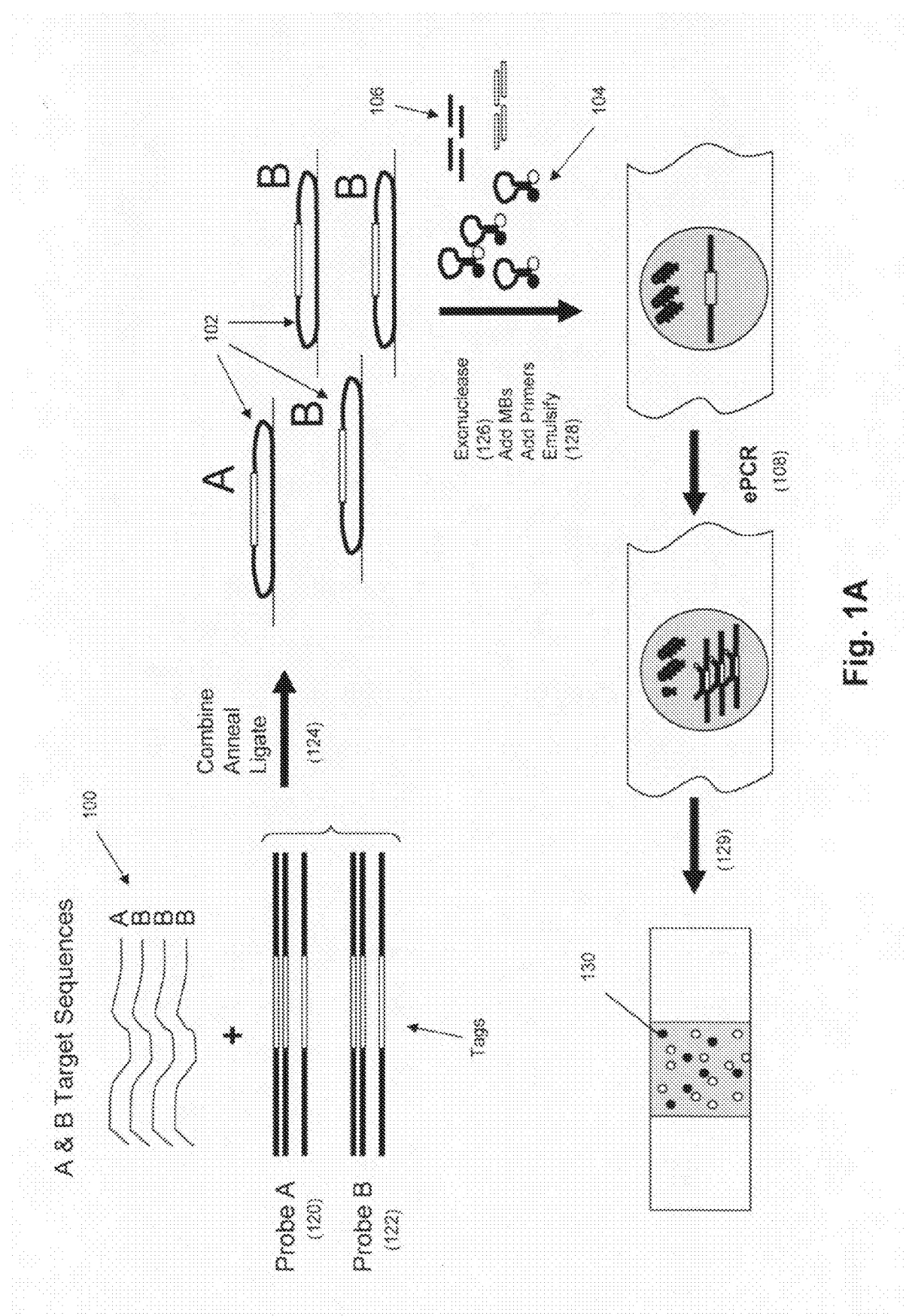
FIGS. 1A-1B diagrammatically illustrate two embodiments of the invention.

An overview of one embodiment of the method is illustrated in FIG. 1A. Target sequences (100) consisting of sequence A and sequence B in a 1:3 ratio are combined with Probe A (120) and Probe B (122), which are specific for sequence A and sequence B, respectively. In this embodiment, Probe A and B are circularizable probes, such that when combined under annealing conditions (124) such a probe anneals to its target in the presence of a ligase, the ends of the probe are ligated together to form a single stranded circular DNA (102), which is an example of a selectable probe. The reaction mixture containing circular DNAs (102) is treated with an exonuclease (126) so that all non-circularized polynucleotides are destroyed, after which primers (106), other amplification reaction components (128), and signal generating components are added. In one embodiment, the signal generating components comprise a mixture of molecular beacons (104), such that there is a molecular beacon that generates a different optical signal for each different oligonucleotide tag. The resulting mixture is combined with an oil and then sonicated or vortexed to form an emulsion such that micelles of the emulsion on average contain one or fewer selectable probes. As the selectable probes are amplified, e.g. in an emulsion PCR (108), the molecular beacons specific for the oligonucleotide tags of the amplified sequences start to generate a unique optical signal within each micelle (130). At the completion of the amplification, a sample of the reaction mixture is analyzed (129), e.g. by imaging a sample disposed on a slide under a microscope, to determine the numbers of micelles generating each of the different optical signals, thereby providing a digital macroscopic readout of the ratio of the different target polynucleotides present in the original sample.

Figure 1B:
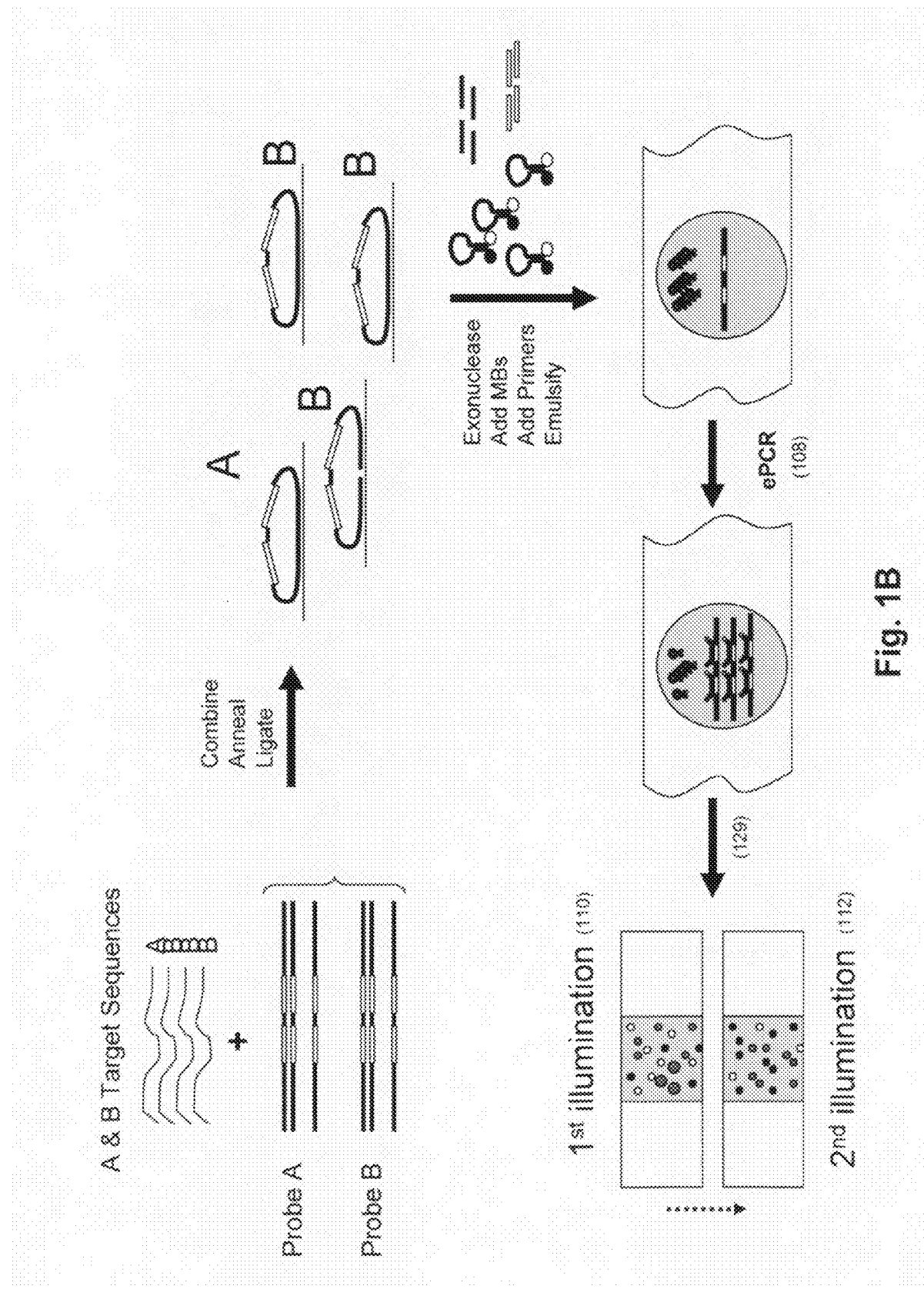

Higher levels of multiplexing may be achieved in the above embodiment by employing multiple oligonucleotide tags in each nucleic acid probe, as exemplified in FIG. 1B. In this embodiment, molecular beacons are employed that have fluorescent moieties with separate absorption bands so that multiple molecular beacons can be detected on the same target sequence by successive illumination with different light beams having wavelengths corresponding to the different absorption bands of the fluorophors. Thus, when a first fluorophor of a first molecular beacon is excited (by $1^{st}$ illumination (110)), only it will generate a fluorescent signal. A second molecular beacon having a second fluorophor on the same amplified target will not fluoresce. After a first signal is detected, a second optical signal is then generated by illuminating the mixture with a beam ($2^{nd}$ illumination (112)) corresponding to the absorption band of the second fluorophor. Thus, each micelle will generate two optical signals from which the identity of its corresponding target polynucleotide is determined.

Figure 2A:
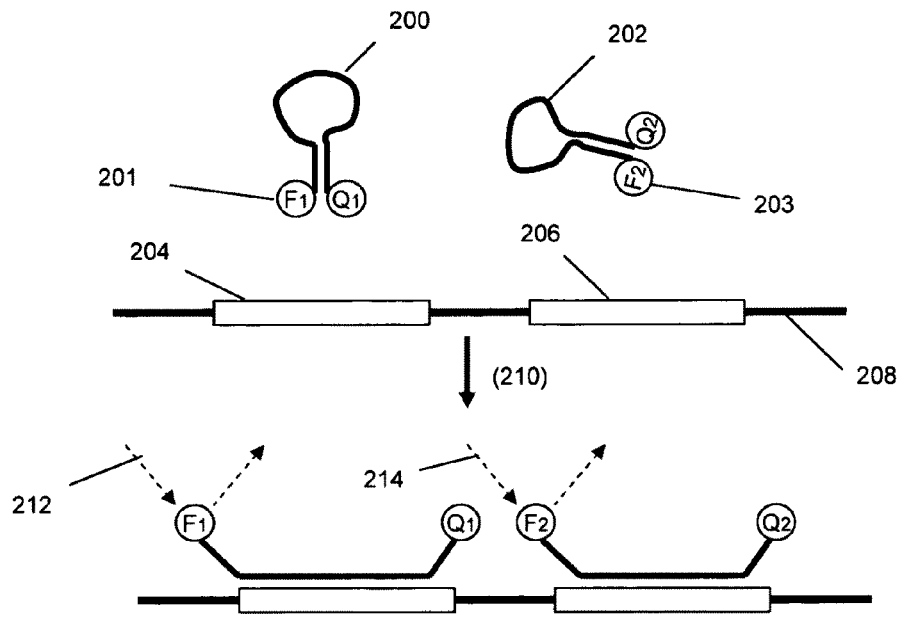
FIGS. 2A-2B illustrate the concept of sequentially illuminated labels.
Figure 2B:
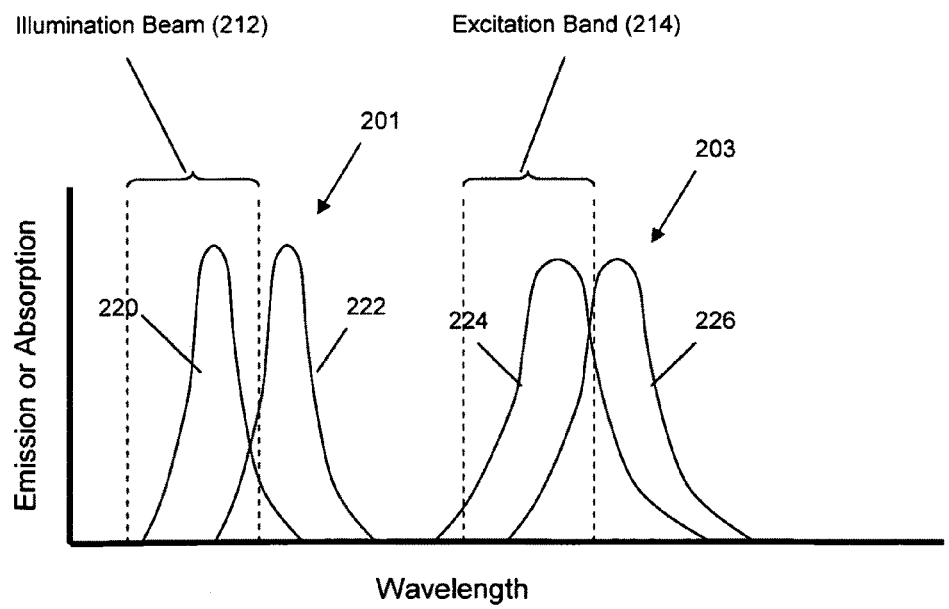

The concept of sets of fluorescent probes having separate absorption bands for sequential excitation is described in Goldberg et al, U.S. patent publication, 2008/0212069A1, and is summarized in FIGS. 2A and 2B for molecular beacons. The use of multiple oligonucleotide tags for higher levels of is further illustrated in FIGS. 3A-3C. In FIG. 2A, molecular beacons (200) and (202) have different fluorescent labels $F_1$ (201) and $F_2$ (203), respectively, which are both in a quenched configuration at the top of the figure. Beacons (200) and (202) are specific for tags (204) and (206), respectively, within probe (208) (or amplicon thereof). In FIG. 2B, the characteristics of the fluorescent labels, such as (201) and (203), and illumination beams are illustrated for sequential illumination. Absorption band (220) and emission band (222) for label (201) and absorption band (224) and emission band (226) of label (203) are spectrally spaced so that label (201) may be excited by illumination beam (212) with bandwidth (230) without affecting label (203). Likewise, label (203) may be excited by illumination beam (214) with bandwidth (232) without affecting label (201).

Figure 3A:
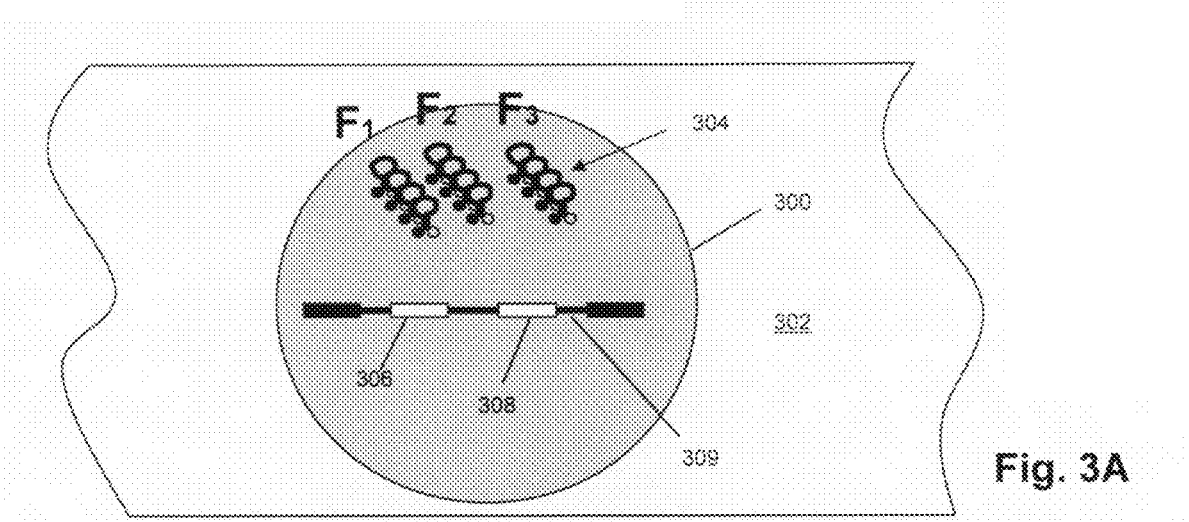
FIGS. 3A-3C illustrate the detection of multiple molecular beacons in micelles
Figure 3B:
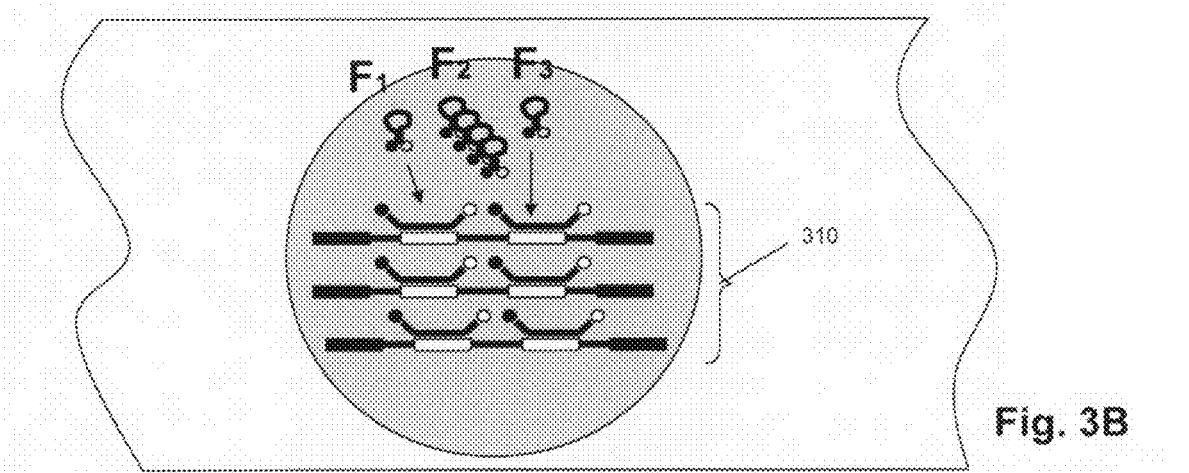
Figure 3C:
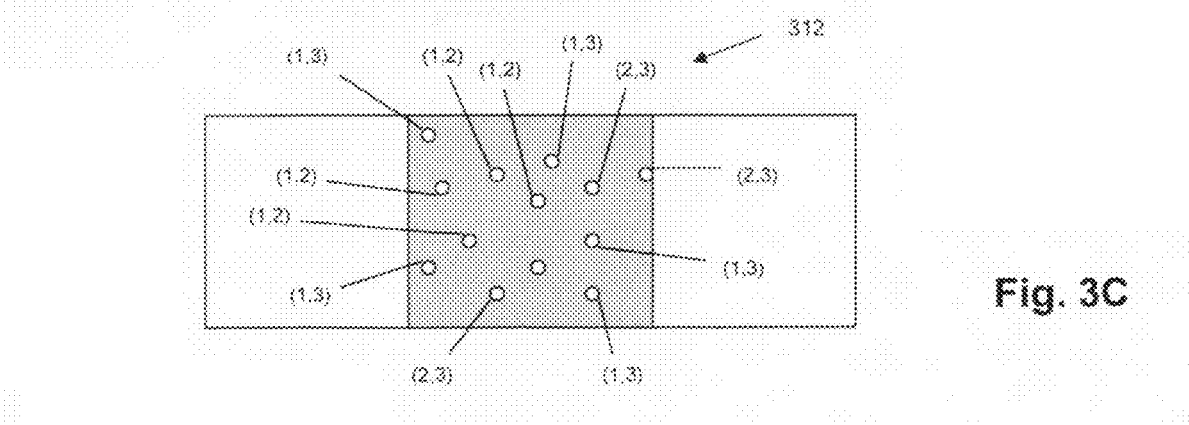

FIGS. 3A-3C illustrate how sequential illumination with two excitation bands and three different possible labels may increase the number of sequences that may be detected. Roughly the increase in targets that may be detected simply equals the number of different pairs that may be selected from a set of three labels, with replacement. That is, if three labels are capable of emitting signals a, b, and c, respectively. Then, the number of pairs (with replacement) is the set (a,a), (b,b), (c,c), (a,b), (a,c), and (b,c). In FIG. 3A, micelle (300) in oil (302) contains three sets of molecular beacons (304) having fluorescent labels F1, F2, and F3, respectively. Probe (309) contains tag complements (306) and (308) of tags contained in molecular beacons F1 and F3. As probe (309) produces amplicon (310) molecular beacons F1 and F3 bind to the tag complements thereby de-quenching their respective labels. The micelles may then be illuminated twice such that each micelle containing a probe amplicon will emit two signals from which its target probe may be identified.

Detection of Micelles

As mentioned above, micelles color coded in accordance with the invention can be counted in a variety of ways, including by flow cytometry and by image analysis using slide-based microscopes. Guidance for using a flow cytometer for implementing the methods of the invention is provided in the following references: *Flow Cytometry: A Practical Approach*, $2^{nd}$ ed., M. G. Ormerod (ed.), Oxford University Press, 1997; *Handbook of Flow Cytometry Methods*, J. Paul Robinson (ed.), John Wiley & Sons (1993); *Current Protocols in Cytometry*, J. Paul Robinson (ed.), John Wiley & Sons (October 1997, with periodic updates); *Becton Dickinson Cytometry Source Book*, Becton Dickinson Immunocytometry Systems (1998, with periodic updates) (San Jose, Calif.), the disclosures of which are incorporated by reference.

Exemplary microscopes for slide-based analysis of samples include an iCyte™ Automated Imaging Cytometer (CompuCyte Corp., Cambridge, Mass.) (e.g. Kamensky et al, Cytometry, 12A: 381 (1991)); an Axioplan 2 MOT microscope (Carl Zeiss, Goettingen, Germany), e.g. equipped with 100 W Mercury lamp, 12 bit Axiocam CCD camera, and motorized object desk and filter changer; or like systems.

In one aspect, colored micelles of the invention may be detected and counted using a low-cost instrument as describe in Goldberg et al, U.S. patent publication 2008/0212069, which in incorporated herein by reference. Briefly, the disclosed instrument provides a means for measuring and counting cells, micelles, particles, and/or analytes in a sample by sequentially illuminating the sample with illumination beams having different wavelength ranges that correspond to the excitation bands of labels directly or indirectly bound or attached to the analytes, cells, or particles in the sample. After each illumination in such a sequence, optical signals are collected to form an image, so that a set of images are formed each containing image data that is analyzed to provide counts and/or measurements of the population of cells, particles, and/or analytes. In one aspect, a plurality of illumination beams is employed that have substantially non-overlapping wavelength ranges. Such plurality of illumination beams may be in the range of from 2 to 6, or in the range of from 2 to 4, or in the range of from 2 to 3. A plurality of illumination beams may be generated by a variety of methods and apparatus available to those of ordinary skill, including by lasers, filament and arc lamps, and the like. In one embodiment, illumination beams are generated using light emitting diodes (LEDs), or like solid state devices. Exemplary LED light sources include Luxeon™ LEDs that have wavelength peaks in green (530 nm), cyan (505 nm), blue (470 nm), and royal blue (455 nm), commercially available from Lumileds Lighting LLC (San Jose, Calif.). Guidance in selecting particular LEDs for use with the invention is widely available in the technical literature, such as Luxeon Star Technical Data Sheet DS23 (Philips Lumileds Lighting Company, San Jose, 2006); Luxeon Star V Technical Data Sheet DS30 (Lumileds Lighting, U.S., LLC, San Jose, Calif., Sep. 20, 2004); and the like. Usually, light sources are used with conventional filters and other optical components for generating illumination beams of desired wavelength ranges and intensity distributions.

A wide variety of optical systems can be employed with the invention. Generally, such systems provide one or more illumination beams for sequentially illuminating a sample in distinct wavelength ranges, an image collection device for recording image data from the illuminated sample, and a controller that controls the operation of the illumination beams and image collection device so that image data sets are sequentially collected.

Figure 5:
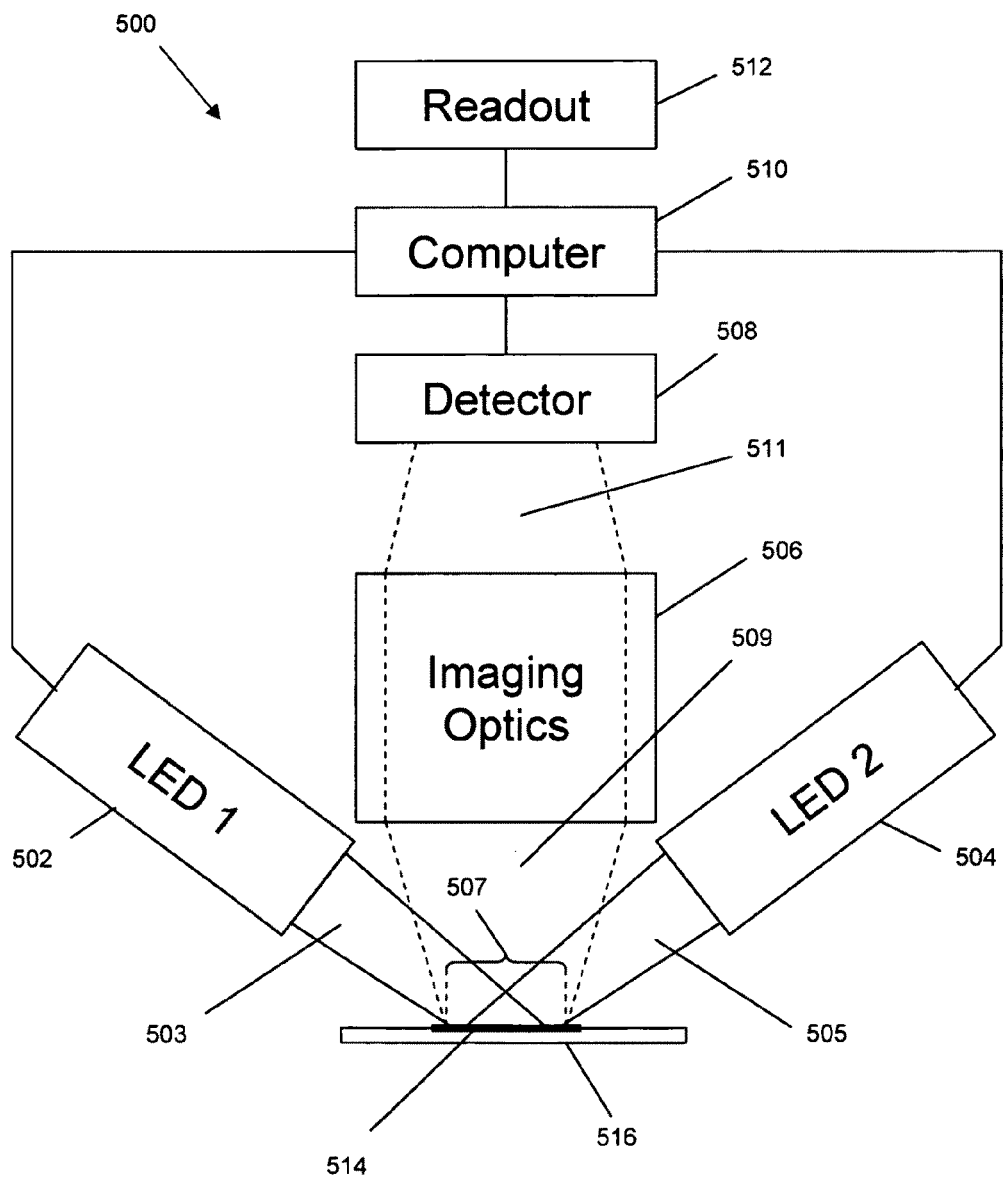
FIG. 5 diagrammatically illustrates a slide-based instrument for detecting and counting colored micelles generated by the invention.

In one aspect, the invention includes a system comprising an image collection device used in concert with sets of differentially excitable dyes attached to probes specific for cell, particles, or analytes of interest in a sample. In other words, such a system comprises an apparatus of the following components for imaging samples or specimens labeled with a plurality differentially excitable labels: (a) multiple light sources each capable of illuminating the specimen with an illumination beam having a distinct wavelength band; (b) a controller coupled to the multiple light sources for successively directing the illumination beam of each light source onto the specimen so that each of the plurality of differentially excitable labels is successively caused to emit an optical signal within the same wavelength band; and (c) an optical system capable of collecting such emitted optical signals and forming successive images corresponding thereto on a light-responsive surface to form successive sets of image data. One embodiment of the above apparatus is illustrated in FIG. 5. System (500) comprises several components, including a plurality of light sources, shown as LED 1 (502) and LED 2 (504), for sequentially illuminating observation area (507) of sample (514) disposed on or in sample platform (516), imaging optics (506) for collecting optical signals (509) generated from probes in and/or on the sample in response to illumination beams (503) and (505) and for directing (511) the collected signals to detector (508), which comprises a light-responsive surface, such as a CCD or CMOS element, on which optical signals (509) form an image and from which successive sets of image data are recorded. Preferably, operation of system (500) is under the control of computer (510) that (a) controls the timing and duration of illumination beams (503) and (505), (b) controls detector (508) for collecting and transferring image data to one or more databases, (c) analyzes image data to produce a readout for readout component (512), and like operations. Sample platform (516) may vary widely in design and functional capabilities, but generally requires that a sample be disposed in a substantially planar geometry that is consistent with collecting a plurality of optical signals in parallel and forming an image on a detector. Preferably, a sample disposed on sample platform (516) is static and not flowing or moving; or if motion is present, it is sufficiently slow that successive images may be collected that are capable of alignment during image analysis. Sample platform (516) may comprise conventional microscope slides, sample chambers or cuvettes used in microscopy, culture plates, microfluidic devices, or the like. In one aspect, described more fully below, sample platform (516) comprises a disposable cuvette that is designed for detection of non-red cell components in whole blood. In another aspect, sample platform (516) comprises a cuvette having a sample chamber with a geometry that permits a known volume to be surveyed whenever such cuvette is used with system (500). In one embodiment, such a sample chamber has a substantially planar geometry wherein (a) a floor (or bottom wall) and a ceiling (or top wall) are parallel to one another and (preferably) perpendicular to the minimal light path to imaging optics (506) and (b) the perpendicular distance between the top and bottom walls is substantially equivalent to the diameter of the cells or particles being detected. Whenever such sample chamber is disposed in observation area (507), which is known or determinable, the cells or particles will be in a known (or determinable) volume, thereby permitting concentrations of the particles or cells to be measured. "Substantially equivalent" in reference to the perpendicular distance, or dimension, between the top and bottom walls of a sample chamber means that, in a whole blood sample, optical signals from non-red cells or particles in observation area (507) are detectable. In other words, a layer of red blood cells (or other debris) that may be between a labeled cell or particle and the top wall of the chamber does not completely obstruct transmission of optical signals. In one aspect, where white blood cells are labeled and detected, such as CD4+ cells, the perpendicular distance between a top wall and a bottom wall is in the range of from 40 to 120 μm, or in the range of from 50 to 100 μm. The nature of readout component (512) may vary widely from a simple numerical display to an information-rich graphic user interface. In one embodiment, a simple numerical readout is provided by readout component (512) that gives counts of one or more predetermined cell or particle types. In another embodiment, readouts comprise concentrations of or one or more predetermined cell or particle types. And in still another embodiment, readouts comprise simple "yes or no" indicators as to whether threshold levels (e.g. counts or concentrations) of cells, particles, or other analytes have or have not been passed.

Tags and Probes for Use with the Invention

In one aspect, the invention employs minimally cross-hybridizing sets of oligonucleotide tags in the construction of probes and molecular beacons, such as disclosed in Brenner et al, U.S. Pat. No. 5,846,719; Mao et al (cited above); Fan et al, International patent publication WO 2000/058516; Morris et al, U.S. Pat. No. 6,458,530; Morris et al, U.S. patent publication 2003/0104436; Church et al, European patent publication 0 303 459; Huang et al, U.S. Pat. No. 6,709,816; which references are incorporated herein by reference. The sequences of oligonucleotides of a minimally cross-hybridizing set differ from the sequences of every other member of the same set by at least two nucleotides, and more preferably, by at least three nucleotides. Thus, each member of such a set cannot form a duplex with the complement of any other member with less than two mismatches, or three mismatches, or more, as the case may be. Preferably, perfectly matched duplexes of tags (for example, in a probe) and tag complements (for example, in molecular beacons) of the same minimally cross-hybridizing set have approximately the same stability, especially as measured by melting temperature. Preferably, oligonucleotide tags and tag complements are selected to have similar duplex or triplex stabilities to one another so that perfectly matched hybrids have similar or substantially identical melting temperatures. This permits mis-matched tag complements to be more readily distinguished from perfectly matched tag complements in the hybridization steps, e.g. by washing under stringent conditions. Guidance for carrying out such selections is provided by published techniques for selecting optimal PCR primers and calculating duplex stabilities, e.g. Rychlik et al, Nucleic Acids Research, 17: 8543-8551 (1989) and 18: 6409-6412 (1990); Breslauer et al, Proc. Natl. Acad. Sci., 83: 3746-3750 (1986); Wetmur, Crit. Rev. Biochem. Mol. Biol., 26: 227-259 (1991); and the like. A minimally cross-hybridizing set of oligonucleotides can be screened by additional criteria, such as GC-content, distribution of mismatches, theoretical melting temperature, and the like, to form a subset which is also a minimally cross-hybridizing set.

In one aspect, hybridization-based assays include circularizing probes, such as padlock probes, rolling circle probes, molecular inversion probes, linear amplification molecules for multiplexed PCR, and the like, e.g. padlock probes being disclosed in U.S. Pat. Nos. 5,871,921; 6,235,472; 5,866,337; and Japanese patent JP 4-262799; rolling circle probes being disclosed in Aono et al, JP-4-262799; Lizardi, U.S. Pat. Nos. 5,854,033; 6,183,960; 6,344,239; molecular inversion probes being disclosed in Hardenbol et al (cited above) and in Willis et al, U.S. patent publication 2004/0101835; and linear amplification molecules being disclosed in Faham et al, U.S. patent publication 2003/0104459; all of which are incorporated herein by reference. Such probes are desirable because non-circularized probes can be digested with single stranded exonucleases thereby greatly reducing background noise due to spurious amplifications, and the like. In the case of molecular inversion probes (MIPs), padlock probes, and rolling circle probes, constructs for generating labeled target sequences are formed by circularizing a linear version of the probe in a template-driven reaction on a target polynucleotide followed by digestion of non-circularized polynucleotides in the reaction mixture, such as target polynucleotides, unligated probe, probe concatatemers, and the like, with an exonuclease, such as exonuclease I.

Figure 4:
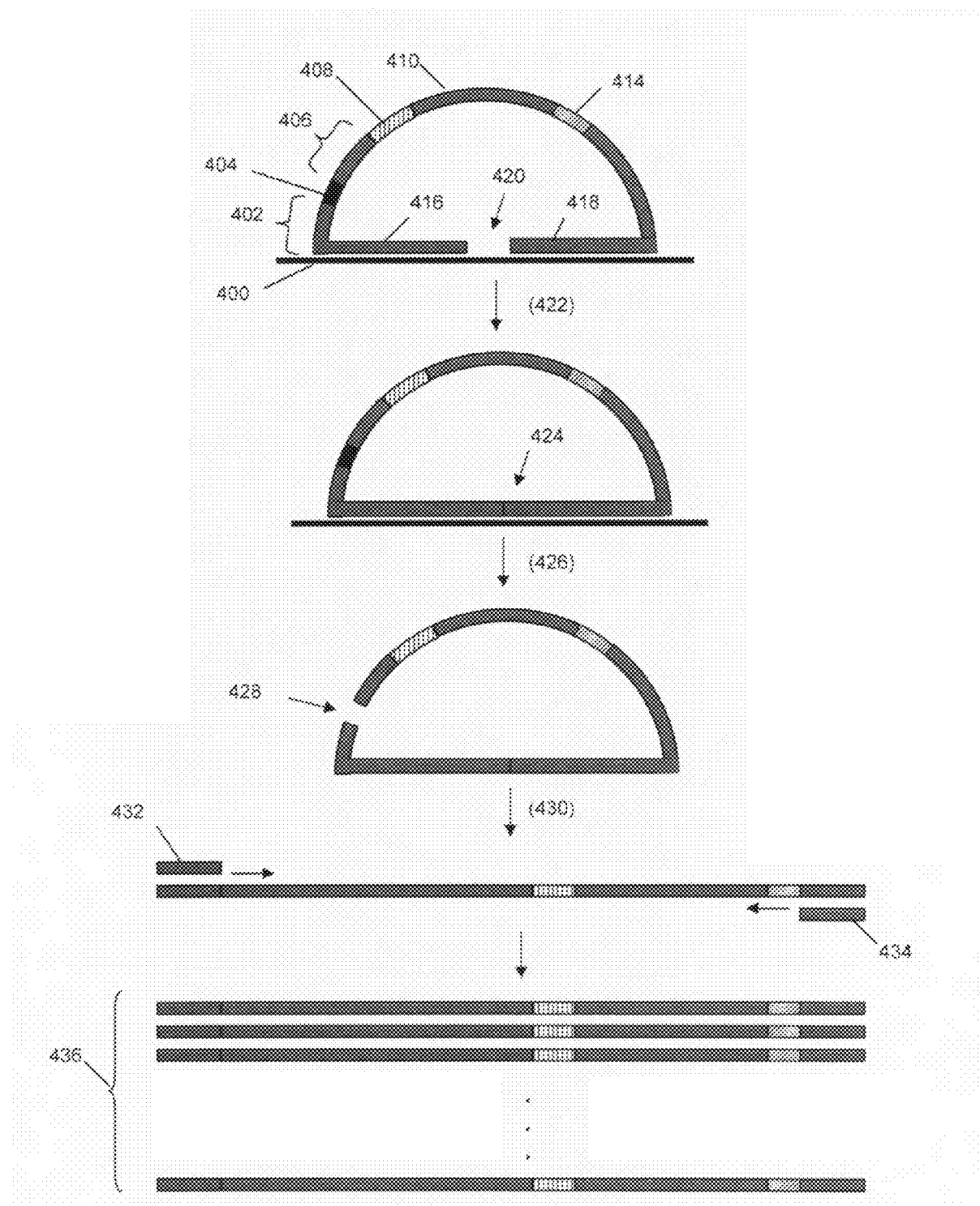
FIG. 4 illustrates a circularizable probe that may be used with the invention.

FIG. 4 illustrates a molecular inversion probe and how it can be used to generate an amplicon after interacting with a target polynucleotide in a sample. A linear version of the probe is combined with a sample containing target polynucleotide (400) under conditions that permit target-specific region 1 (416) and target-specific region 2 (418) to form stable duplexes with complementary regions of target polynucleotide (400). The ends of the target-specific regions may abut one another (being separated by a "nick") or there may be a gap (420) of several (e.g. 1-10 nucleotides) between them. In either case, after hybridization of the target-specific regions, the ends of the two target specific regions are covalently linked by way of a ligation reaction or an extension reaction followed by a ligation reaction, i.e. a so-called "gap-filling" reaction. The latter reaction is carried out by extending with a DNA polymerase a free 3' end of one of the target-specific regions so that the extended end abuts the end of the other target-specific region, which has a 5' phosphate, or like group, to permit ligation. In one aspect, a molecular inversion probe has a structure as illustrated in FIG. 4. Besides target-specific regions (416 and 418), in sequence such a probe may include first primer binding site (402), cleavage site (404), second primer binding site (406), first tag-adjacent sequences (408) (usually restriction endonuclease sites and/or primer binding sites) for tailoring one end of a labeled target sequence containing oligonucleotide tag (410), and second tag-adjacent sequences (414) for tailoring the other end of a labeled target sequence. Alternatively, cleavage-site (404) may be added at a later step by amplification using a primer containing such a cleavage site. In operation, after specific hybridization of the target-specific regions and their ligation (422), the reaction mixture is treated with a single stranded exonuclease that preferentially digests all single stranded nucleic acids, except circularized probes. After such treatment, circularized probes are treated (426) with a cleaving agent that cleaves the probe between primer (402) and primer (406) so that the structure is linearized (430). Cleavage site (404) and its corresponding cleaving agent is a design choice for one of ordinary skill in the art. In one aspect, cleavage site (404) is a segment containing a sequence of uracil-containing nucleotides and the cleavage agent is treatment with uracil-DNA glycosylase followed by heating. After the circularized probes are opened, the linear product is amplified, e.g. by ePCR using primers (432) and (434), to form amplicons (436).

Emulsion PCR (ePCR) protocols to form clonal populations of templates on beads are disclosed in Dressman et al (2003), Proc. Natl. Acad. Sci., 100: 8817-8822; Li et al (2006), Nature Methods, 3: 95-97; Shendure et al (2005), Science, 309: 1728-1732; Berka et al, U.S. patent publication 2005/0079510; and Tillett et al, International patent publication WO 03/106698, which are incorporated by reference for their guidance in implementing emulsion PCR. Briefly, after an amplicon is generated in, an aqueous phase solution containing the amplicon, or a portion thereof, e.g. 10-100 pg, and amplification reagents, e.g. for PCR or like technique, is mixed with a light oil, such as mineral oil, so that micro-droplets of aqueous phase solution forms in the oil. The composition of these reagents are selected to maximize the formation of such micro-droplets containing a single target polynucleotide. Once such an emulsion is formed, conditions are selected for implementing an amplification reaction, such as PCR, to amplify the target in the presence of molecular beacons. Further disclosure of emulsion PCR is provided in the following references, which are incorporated by reference: Tawfik and Griffiths, "Man-made cell-like compartments for molecular evolution," Nature Biotechnology, 16: 652-656 (1998); Musyanovych et al, "Miniemulsion droplets as single molecule nanoreactors for polymerase chain reaction," Biomacromolecules, 6: 1824-1828 (2005); Lee et al, "Single-molecule enzymology of chymotrypsin using water-in-oil emulsion," Biophysical J., 88: 4303-4311 (2005); Mastobattista et al, "High-throughput screening of enzyme libraries: in vitro evolution of a β-galactosidase by fluorescence-activated sorting of double emulsions," Chemistry & Biology, 12: 1291-1300 (2005).

The construction and use of molecular beacons are disclosed in the following references, which are incorporated by reference: Tyagi and Kramer, "Molecular beacons: probes that fluoresce upon hybridization," Nature Biotechnology, 14: 303-308 (1996); Marras et al, "Multiplex detection of single-nucleotide variations using molecular beacons," Genet. Anal., 14: 151-156 (1999); Tyagi et al, "Multicolor molecular beacons for allele discrimination," Nature Biotechnology, 16: 49-53 (1998).

Sample or Specimen Preparation

Samples or specimens containing target polynucleotides may come from a wide variety of sources for use with the present invention, including cell cultures, animal or plant tissues, patient biopsies, environmental samples, or the like. Samples are prepared for assays of the invention using conventional techniques, which typically depend on the source from which a sample or specimen is taken.

Samples or specimens are collected so as to minimize the chance of contamination of the sample or specimen by external elements, or the environment by the sample or specimen if it contains hazardous components. Generally, this is carried out by introducing a sample for analysis, e.g. tissue, blood, saliva, etc., directly into a sample collection chamber within a fluidly closed system. Typically, the prevention of cross-contamination of the sample may be accomplished by directly injecting the sample into the sample collection chamber through a sealable opening, e.g. an injection valve, or a septum. Generally, sealable valves are preferred to reduce any potential threat of leakage during or after sample injection. In addition to the foregoing, the sample collection portion of the device may also include reagents and/or treatments for neutralization of infectious agents, stabilization of the specimen or sample, pH adjustments, and the like. Stabilization and pH adjustment treatments may include, e.g. introduction of heparin to prevent clotting of blood samples, addition of buffering agents, addition of protease or nuclease inhibitors, preservatives and the like. Such reagents may generally be stored within the sample collection chamber of the device or may be stored within a separately accessible chamber, wherein the reagents may be added to or mixed with the sample upon introduction of the sample into the device. These reagents may be incorporated within the device in either liquid or lyophilized form, depending upon the nature and stability of the particular reagent used.

Prior to carrying out amplification reactions on a sample, it will often be desirable to perform one or more sample preparation operations upon the sample. Typically, these sample preparation operations will include such manipulations as extraction of intracellular material, e.g. nucleic acids from whole cell samples, viruses and the like. One or more of these various operations may be readily incorporated into fluidics or microfluidics device used with the present invention.

For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g. denaturation of contaminating (DNA binding) proteins, purification, filtration, desalting, and the like. Liberation of nucleic acids from the sample cells or viruses, and denaturation of DNA binding proteins may generally be performed by chemical, physical, or electrolytic lysis methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within a sample preparation chamber, a separate accessible chamber, or may be externally introduced.

Physical methods may be used to extract the nucleic acids and denature DNA binding proteins. Wilding et al. U.S. Pat. No. 5,304,487, incorporated herein by reference in its entirety for all purposes, discusses the use of physical protrusions within microchannels or sharp edged particles within a chamber or channel to pierce cell membranes and extract their contents. Combinations of such structures with piezoelectric elements for agitation can provide suitable shear forces for lysis. Such elements are described in greater detail with respect to nucleic acid fragmentation, below. More traditional methods of cell extraction may also be used, e.g. employing a channel with restricted cross-sectional dimension which causes cell lysis when the sample is passed through the channel with sufficient flow pressure. Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to perform cell lysis/extraction, including, e.g. subjecting cells to ultrasonic agitation, or forcing cells through small apertures, thereby subjecting the cells to high shear stress resulting in rupture.

Following extraction, it will often be desirable to separate the nucleic acids from other elements of the crude extract, e.g. denatured proteins, cell membrane particles, salts, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g. by binding the nucleic acids to a solid phase and washing away the contaminating salts or performing gel filtration chromatography on the sample, passing salts through dialysis membranes, and the like. Suitable solid supports for nucleic acid binding include, e.g. diatomaceous earth, silica (i.e., glass wool), or the like. Suitable gel exclusion media, also well known in the art, may also be readily incorporated into the devices of the present invention, and is commercially available from, e.g. Pharmacia and Sigma Chemical Co.

The isolation and/or gel filtration/desalting may be carried out in an additional chamber, or alternatively, the particular chromatographic media may be incorporated in a channel or fluid passage leading to a subsequent reaction chamber. Alternatively, the interior surfaces of one or more fluid passages or chambers may themselves be derivatized to provide functional groups appropriate for the desired purification, e.g. charged groups, affinity binding groups and the like, i.e. poly-T oligonucleotides for mRNA purification. Alternatively, desalting methods may generally take advantage of the high electrophoretic mobility and negative charge of DNA compared to other elements. Electrophoretic methods may also be utilized in the purification of nucleic acids from other cell contaminants and debris. In one example, a separation channel or chamber of the device is fluidly connected to two separate "field" channels or chambers having electrodes, e.g. platinum electrodes, disposed therein. The two field channels are separated from the separation channel using an appropriate barrier or "capture membrane" which allows for passage of current without allowing passage of nucleic acids or other large molecules. The barrier generally serves two basic functions: first, the barrier acts to retain the nucleic acids which migrate toward the positive electrode within the separation chamber; and second, the barriers prevent the adverse effects associated with electrolysis at the electrode from entering into the reaction chamber (e.g. acting as a salt junction). Such barriers may include, e.g. dialysis membranes, dense gels, PEI filters, or other suitable materials. Upon application of an appropriate electric field, the nucleic acids present in the sample will migrate toward the positive electrode and become trapped on the capture membrane. Sample impurities remaining free of the membrane are then washed from the chamber by applying an appropriate fluid flow. Upon reversal of the voltage, the nucleic acids are released from the membrane in a substantially purer form. The field channels may be disposed on the same or opposite sides or ends of a separation chamber or channel, and may be used in conjunction with mixing elements described herein, to ensure maximal efficiency of operation. Further, coarse filters may also be overlaid on the barriers to avoid any fouling of the barriers by particulate matter, proteins or nucleic acids, thereby permitting repeated use. In a similar aspect, the high electrophoretic mobility of nucleic acids with their negative charges, may be utilized to separate nucleic acids from contaminants by utilizing a short column of a gel or other appropriate matrix or gel which will slow or retard the flow of other contaminants while allowing the faster nucleic acids to pass.

For a number of applications, it may be desirable to extract and separate messenger RNA from cells, cellular debris, and other contaminants. As such, a system of the present invention may, in some cases, include an mRNA purification chamber or channel. In general, such purification takes advantage of the poly-A tails on mRNA. In particular and as noted above, poly-T oligonucleotides may be immobilized within a chamber or channel of the device to serve as affinity ligands for mRNA. Poly-T oligonucleotides may be immobilized upon a solid support incorporated within the chamber or channel, or alternatively, may be immobilized upon the surface(s) of the chamber or channel itself.

In some applications, such as measuring target polynucleotides in rare metastatic cells from a patient's blood, an enrichment step may be carried out prior to conducting an assay, such as by immunomagnetic isolation. Such isolation or enrichment may be carried out using a variety of techniques and materials known in the art, as disclosed in the following representative references that are incorporated by reference: Terstappen et al. U.S. Pat. No. 6,365,362; Kresse et al. U.S. Pat. No. 6,048,515; Miltenyi et al. U.S. Pat. No. 5,691,208; Radbruch et al. chapter 23, in *Methods in Cell*

Biology, Vol, 42 (Academic Press, New York, 1994); Uhlen et al. *Advances in Biomagnetic Separation* (Eaton Publishing, Natick, 1994); Safarik et al. *J. Chromatography B,* 722:33-53 (1999); Miltenyi et al. *Cytometry,* 11:231-238 (1990); Nakamura et al. *Biotechnol. Prog.,* 17:1145-1155 (2001); Moreno et al. *Urology,* 58:386-392 (2001); Racila et al. *Proc. Natl. Acad. Sci.,* 95:4589-4594 (1998); Zigeuner et al. *J. Urology,* 169:701-705 (2003); Ghossein et al. *Seminars in Surgical Oncology,* 20:304-311 (2001).

Definitions

Generally, terms used herein not otherwise specifically defined have meanings corresponding to their conventional usage in the fields related to the invention, including analytical chemistry, biochemistry, molecular biology, cell biology, microscopy, image analysis, and the like, such as represented in the following treatises: Alberts et al, Molecular Biology of the Cell, Fourth Edition (Garland, 2002); Nelson and Cox, Lehninger Principles of Biochemistry, Fourth Edition (W. H. Freeman, 2004); Murphy, Fundamentals of Light Microscopy and Electronic Imaging (Wiley-Liss, 2001); Shapiro, Practical Flow Cytometry, Fourth Edition (Wiley-Liss, 2003); and the like. "Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, cofactors, scavengers, and the like.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the position and fluorescence intensity of a signal being generated at each hybridization site of the microarray; thus, such a readout may be registered or stored in various ways, for example, as an image of the microarray, as a table of numbers, or the like.

"Sample" means a quantity of material from a biological, environmental, medical, or patient source in which detection or measurement of target nucleic acids is sought. The term "sample" encompasses biological samples, e.g. a quantity of blood, a microbiological culture, or the like; environmental samples, e.g. a soil or water sample; medical samples or specimens, e.g. a quantity of blood or tissue; or the like. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. The terms "sample" and "specimen" are used interchangeably.

"Specific" or "specificity" in reference to the binding of one molecule to another molecule means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least thirty percent. Generally, molecules involved in a specific binding event have areas on their surfaces, and/or in the case of proteins in cavities, giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"Denaturing" conditions or reagents disrupt base-pairing and cause separation of a duplex into single-strands. Denaturing conditions and reagents include heat, basic pH, high salt concentrations and specific denaturants, such as formamide and ammonium hydroxide. "Non-denaturing" conditions allow base-pairing in duplex structures to persist. Non-denaturing conditions typically include low temperature, neutral pH, low salt concentrations, neutral aqueous buffers, and reagents which do not disrupt hydrogen bonding between nucleobases.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g. conditions including temperature of about 5° C. less that the $T_m$ of a strand of the duplex and low monovalent salt concentration, e.g. less than 0.2 M, or less than 0.1 M. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Hybridization" or "annealing" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" or "annealing conditions" will typically include salt concentrations of less than about 1M, more usually less than about 500 mM and less than about 200 mM. Hybridization or annealing temperatures can be as low as 5° C., but are typically greater than 22° C., more typically greater than about 30° C., and preferably in excess of about 37° C. Hybridization and annealing are usually performed under stringent conditions, i.e. conditions selected to minimize the hybridization or annealing of undesired oligonucleotides, polynucleotides, or probes to a target subsequence. Stringent conditions are sequence-dependent and are different in different circumstances. Longer fragments may require higher hybridization temperatures for specific hybridization. Several factors may affect the stringency of hybridization or annealing, including base composition and length of the complementary strands, presence of organic solvents and extent of base mismatching. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "annealing specifically to" or "specifically hybridizing to" or like expressions refer to the binding, duplexing, annealing or hybridizing of a molecule substantially to or only to a particular nucleotide sequence or sequences under stringent conditions when that sequence is present in a complex mixture (e.g., total cellular) DNA or RNA.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. Ligations are usually carried out enzymatically by a ligase to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213. Chemical ligation methods are well known in the art, e.g. Ferris et al, Nucleosides & Nucleotides, 8: 407-414 (1989); Shabarova et al, Nucleic Acids Research, 19: 4247-4251 (1991); and the like. Preferably, enzymatic ligation is carried out using a ligase in a standard protocol. Many ligases are known, and are suitable for use in the invention, e.g. Lehman, Science, 186: 790-797 (1974); Engler et al, DNA Ligases, pages 3-30 in Boyer, editor, The Enzymes, Vol. 15B (Academic Press, New York, 1982); and the like. Preferred ligases include T4 DNA ligase, T7 DNA ligase, *E. coli* DNA ligase, Taq ligase, Pfu ligase, and Tth ligase. Protocols for their use are well known, e.g. Sambrook et al (cited above); Barany, PCR Methods and Applications, 1: 5-16 (1991); Marsh et al, Strategies, 5: 73-76 (1992); and the like. Generally, ligases require that a 5' phosphate group be present for ligation to the 3' hydroxyl of an abutting strand. Particularly efficient ligation takes place when the terminal phosphate of one oligonucleotide and the terminal hydroxyl group of an adjacent second oligonucleotide are annealed together across from their complementary sequences within a double helix, i.e. where the ligation process ligates a "nick" at a ligatable nick site and creates a complementary duplex.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, and a detection system. Microfluidics may further include valves, pumps, and specialized functional coatings on their interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 µm to about 0.1 µm. Microfluidics devices typically have volume capacities in the range of from 1 µL to a few nL, e.g. 10-100 mL. The fabrication and operation of microfluidics devices are well-known in the art as exemplified by the following references that are incorporated by reference: Ramsey, U.S. Pat. Nos. 6,001,229; 6,010, 607; and 6,033,546; Soane et al. U.S. Pat. No. 6,054,034; Nelson et al. U.S. Pat. No. 6,613,525; Maher et al. U.S. Pat. No. 6,399,952; Ricco et al. Int'l Patent Publication No. WO 02/24322; Bjornson et al. Int'l Patent Publication No. WO 99/19717; Sia et al. *Electrophoresis*, 24:3563-3576 (2003); Unger et al. *Science*, 288:113-116 (2000); Enzelberger et al. U.S. Pat. No. 6,960,437.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. Reaction volumes typically range from a few hundred nanoliters, e.g. 200 nL, to a few hundred µL, e.g. 200 µL. "Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A method of determining relative amounts of a plurality of target polynucleotides in a sample, the method comprising the steps of:

combining in a reaction mixture the plurality of target polynucleotides and a plurality of different nucleic acid probes each specific for a different target polynucleotide so that selectable nucleic acid probes are formed, such that the selectable nucleic acid probes are in substantially the same relative amounts as the plurality of target polynucleotides and are resistant to at least one nuclease activity, wherein each different nucleic acid probe comprises a different oligonucleotide tag;

treating the reaction mixture with one or more nuclease activities so that substantially all nucleic acid probes that do not form selectable probes are digested;

amplifying the selectable nucleic acid probes in an emulsion amplification reaction, the emulsion amplification reaction comprising micelles that each comprise on average one or fewer selectable nucleic acid probes, amplification reaction components, and a signal generating component specific for each different oligonucleotide tag, such that an optical signal specific for such oligonucleotide tag is generated whenever a selectable nucleic acid probe containing such oligonucleotide tag is amplified; and determining numbers of micelles having optical signals specific for each different oligonucleotide tag in a sample of the emulsion amplification reaction to determine the relative amounts of the plurality of target polynucleotides.

2. The method of claim 1 wherein said emulsion amplification reaction is an emulsion polymerase chain reaction.

3. The method of claim 1 wherein said selectable nucleic acid probes are circularizing probes.

4. The method of claim 3 wherein said selectable nucleic acid probes are resistant to exonuclease activity.

5. The method of claim 1 wherein said signal generating component generates a signal proportional to said amplification of said selectable nucleic acid probe.

6. The method of claim 5 wherein said signal generating component is a molecular beacon.

7. The method of claim 1 wherein said plurality of said target polynucleotides is between two and four.

8. The method of claim 3 wherein said circularizing probe is a molecular inversion probe.

* * * * *